United States Patent [19]
Woodman

[11] 4,019,060
[45] Apr. 19, 1977

[54] FLUORESCENCE LOCATING SYSTEM AND METHOD

[75] Inventor: Douglas P. Woodman, Menlo Park, Calif.

[73] Assignee: GTE Sylvania Incorporated, Mountain View, Calif.

[22] Filed: Oct. 3, 1975

[21] Appl. No.: 619,388

[52] U.S. Cl. .................... 250/461 R; 250/203 R; 250/458
[51] Int. Cl.² ..................................... G01N 21/38
[58] Field of Search ............ 250/458, 461 B, 427, 250/203, 302; 209/111.6

[56] References Cited
UNITED STATES PATENTS

| | | | |
|---|---|---|---|
| 3,617,744 | 11/1971 | Irish | 250/461 |
| 3,685,650 | 8/1972 | Walther et al. | 209/111.6 X |
| 3,770,349 | 11/1973 | Legorreta-Sanchez | 250/461 B |
| 3,811,777 | 5/1974 | Chance | 250/458 X |
| 3,935,922 | 2/1976 | Cooper et al. | 250/461 X |

Primary Examiner—Archie R. Borchelt
Attorney, Agent, or Firm—John F. Lawler; Norman J. O'Malley; Theodore C. Jay, Jr.

[57] ABSTRACT

A system for identifying and locating objects of known chemical composition and discriminating against a background having a different chemical composition comprises a source of radiation for illuminating the object and the background and a receiver responsive solely to the fluorescent radiation from the object. The receiver comprises a filter which passes radiation from the object and a photodetector array which receives the filter output and produces an output containing the coordinates of the location of the received signal or signals on the array. This location information is applied to utilization apparatus which may comprise a marking mechanism which marks the location of the object on the background or automatic tracking apparatus which tracks the object of interest or counter apparatus which identifies the quantity of such objects that are illuminated.

The invention also comprehends the method of deriving position data by causing a known substance to fluoresce at wavelengths (centered at $\lambda_0$) different from that of the source which illuminates the substance, filtering out all light but that at the $\lambda_0$ wavelength, directing said $\lambda_0$ light against an array of transducer cells and producing an output having coordinates of the cell receiving the $\lambda_0$ energy, and feeding the output of the array to utilization apparatus.

4 Claims, 5 Drawing Figures

FLUORESCENCE LOCATING SYSTEM AND METHOD

BACKGROUND OF THE INVENTION

This invention relates to detection and tracking systems and techniques and more particularly to an improved optical system and technique for detecting, locating and/or tracking various objects.

The technique of illuminating an object with electromagnetic radiation and receiving such radiations that are reflected from the object as a means of detecting and locating it is well known. One characteristic of radar systems is that the received signal is indicative primarily of the size of the object. The dependence of the received signal on the chemical composition of the object is very weak, and in most situations discrimination of objects based on chemical composition is not possible. Reflections from undesired objects are therefore often indistinguishable from those of desired objects. An example of this problem is ground clutter in land based microwave radar systems. There are applications where use of a radar-like technique to identify a substance on the basis of its composition is both desirable and useful and a need exists for a system capable of deriving such information.

OBJECTS AND SUMMARY OF THE INVENTION

An object of this invention is the provision of an optical system for detecting and locating an object on the basis of the chemical composition of the object.

Another object is the provision of an object detecting and locating system which is capable of discriminating between objects in the field of search on the basis of their chemical composition.

Another object is the provision of a method of identifying and locating objects having a known composition and discriminating against adjacent objects having a different composition.

A more specific object is the provision of a system and method for detecting and locating or tracking an object having one chemical composition and disposed on or located adjacent to an object or objects having other chemical composition.

Still another object is the provision of an optical transmit-and-receive system and method which qualitatively distinguishes between illuminated objects on the basis of their chemical composition and identifies the relative position of a selected object.

These and other objects of the invention are achieved with a system and technique in which objects of interest are optically illuminated with predetermined radiation so as to cause the objects to emit radiations having wavelengths different from that of the illuminating radiation and corresponding to the composition of the objects. Discrimination between desired and undesired objects is achieved with a filter which passes induced radiations from the desired object and blocks off other radiations. The position or location of the desired object is determined by the point of incidence of imaged light on a detector array which feeds the position information to utilization apparatus capable of identifying the location of the object, counting the number of objects in the field of search, and/or providing an input to automatic tracking apparatus for tracking the object.

DESCRIPTION OF PREFERRED EMBODIMENTS

Figure 1:
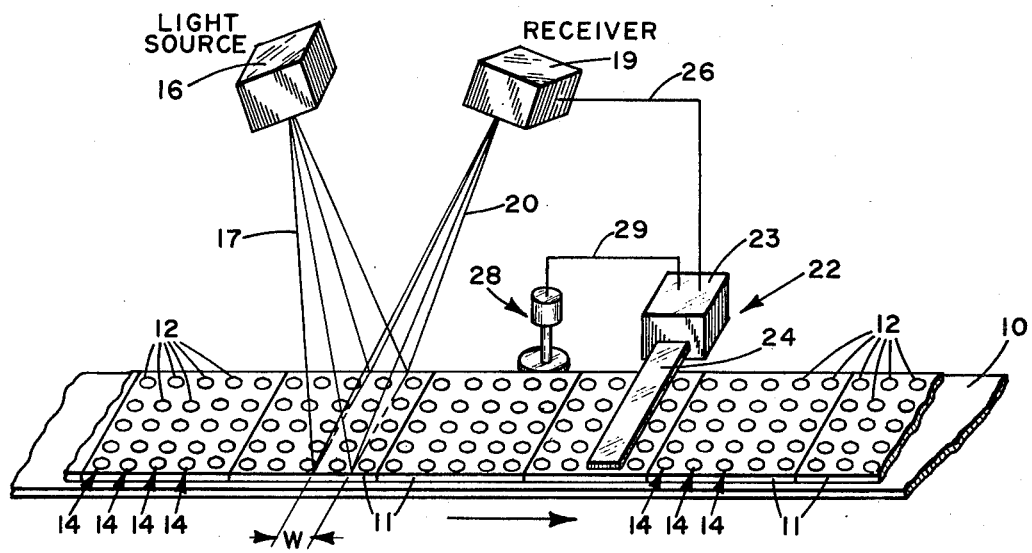
FIG. 1 is a perspective view of a blood sample testing system embodying the invention.
Figure 2:
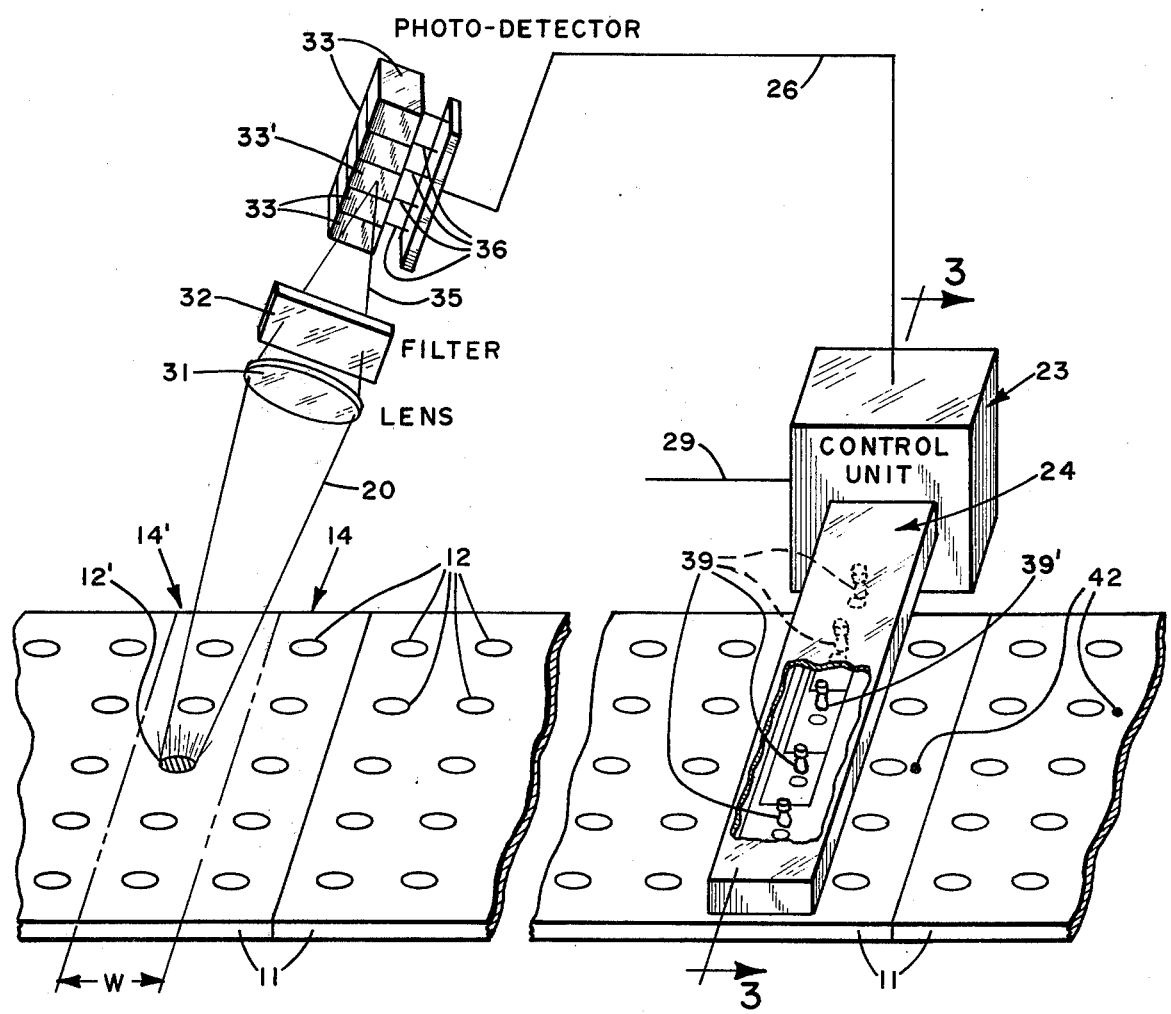
FIG. 2 is an enlarged simplified perspective view similar to FIG. 1 in which some of the system elements are omitted for sake of clarity of description.
Figure 3:
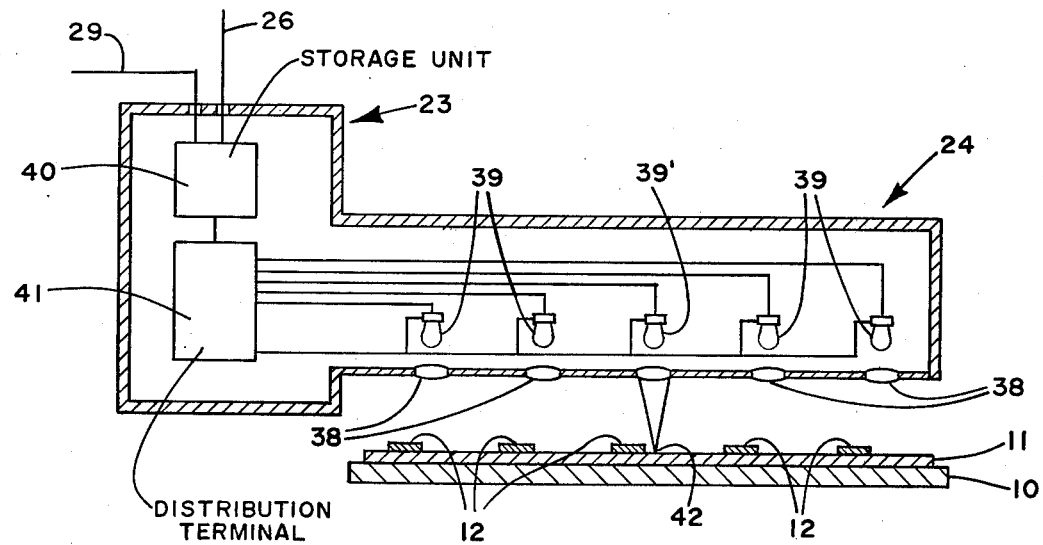
FIG. 3 is a section taken on line 3—3 of FIG. 2 showing the sample marking assembly.

Referring now to the drawings, FIGS. 1, 2 and 3 illustrate somewhat schematically apparatus embodying the invention for detecting and identifying contaminted blood samples and useful in detecting blood poisoning. The apparatus comprises a movable belt 10 on which trays 11 of blood samples 12 are disposed for movement in the direction of the arrow. For convenience of processing by this apparatus, the blood samples are aligned in a succession of columns 14 which extend transversely of the direction of belt movement with each blood sample suitably spaced from other samples in the same and adjacent columns. Each sample may be from a different donor and is so identified by a label or the like, not shown, on the tray. Some of the samples may be contaminated as by lead poisoning or the like which changes the chemical constituency of the sample from that of uncontaminated cells.

In accordance with the invention, a source 16 of light is spaced above belt 10 and directs an output beam 17 on the moving trays 11 so as to illuminate the blood samples 12 thereon. Beam 17 preferably is formed by suitable optical elements, not shown, at source 16 into a shape having the width W of a column 14 of blood samples so as to illuminate one column at a time as the belt moves relative to the beam.

A receiver 19 is similarly disposed above the moving belt and has optical elements for focusing the receiver "beam" 20 on the particular column of samples which is illuminated by the beam 17. This is illustrated in FIG. 1 by the overlapping of transmitter beam 17 and receiver beam 20. Receiver 19 is fixed relative to source 16 so that the belt 10 moves relative to both receiver 19 and source 16.

In order to identify the contaminated blood cells, a marker mechanism 22 is disposed adjacent to and above moving trays 11 and spaced in the direction of movement of the belt from the area of illumination of the blood samples by beam 17. Mechanism 22 comprises a control unit 23 and a marker arm 24 which extends across the full width of the trays transversely of tray movement. Control unit 23 is connected by line 26 to receiver 19 and is responsive to the output of the receiver for marking the contaminated blood cells as described below. In order to synchronize the operation of receiver 19 and marker mechanism 22 with the movement of belt 10, a belt velocity sensor 28 coupled to the belt is electrically connected by line 29 to control unit 23 of the marker mechanism to delay operation of the marker until the contaminated cell has moved under marker arm 24.

Receiver 19 comprises a focusing lens 31, see FIG. 2, an optical filter 32 and an array of photodetector cells 33. Cells 33 have position correlation with the samples 12 in each row 14 so as to provide sample position information in the outputs of the cells. In the embodiments shown, the number of cells 33 in the array is equal to the number of samples 12 in each row 14. Lens 31 focuses radiations from the illuminated column of samples 12 through filter 32 so that any output from the filter is in the form of a beam 35 which converges to dimension smaller than the face area of a cell 33. The outputs of cells 33 are connected by lines 36, respectively, to a terminal block and are transmitted over line 26 to control unit 23 of the marker mechanism so as to maintain position identity of the cell on which beam 35 impinges.

In accordance with this invention, source 16 illuminates column 14', see FIG. 2, of blood samples at a wavelength which causes the blood samples to fluoresce and thus emit radiations at wavelengths corresponding to the chemical composition of the samples. These fluoroescent emissions have a wavelength different from the wavelength of beam 17 from the illuminating source. If one of the blood samples, such as that indicated at 12', is contaminated as a result, for example, of lead poisoning of the donor, that sample fluoresces at a wavelength $\lambda_0$ different from wavelengths of both the source and the fluorosecent radiations of the other non-contaminated samples. Filter 32 has a bandpass which is designed to preferentially transmit the $\lambda_0$ radiation from blood sample 12' to the photodetector array but blocks all other radiations and reflections. Thus photodetector cells 33 both detect the presence of a contaminated sample and are capable of indicating its location on the tray by virtue of the positional coincidence of the energized cell and blood sample.

By way of example, source 16 of the illuminating light may be a dye laser of the type described in an article entitled "High Peak Power 532 Nm Pumped Dye Laser" by E. O. Ammann et al., IEEE Journal of Quantum Electronics, April, 1974, Vol. QE-10, pages 463–465, and having a beam 17 with a wavelength of 424 nanometers (nm). Blood samples contaminated with lead and illuminated by this beam produce a fluorescent emission having a center wavelength $\lambda_0$ equal to 594 nm. Accordingly, filter 32 would be constructed with a bandpass at 594 nm to discriminate against all but the emissions from the contaminated blood sample. Filter 32 may comprise a commercially available absorption filter such as a ROLYN, catalogue No. 65.1325, filter sold by Rolyn Optics Company, 300 Rolyn Place, Arcadia, Calif.

In order to utilize this detection and position capability of receiver 19, marker arm 24 is provided with a plurality of focusing lenses 38, equal to the number of photodetector cells 33 and to the same number of blood samples in each column, and a like number of lamps 39 disposed adjacent to lenses 38, respectively. The outputs of detector cells 33 and velocity sensor 28 are fed via lines 26 and 29, respectively, to a delay or storage unit 40 which delays energization of the particular lamp through a distribution terminal 41 by a time factor corresponding to the separation of the detection and marking points and the belt velocity. By way of example, storage unit 40 may comprise a fixed delay relay. Lenses 38 are positioned relative to the trays and lamps so as to focus the output of the associated lamp to a point adjacent to a blood sample under that lens and to make a visible mark on the tray as indicated by the dots 42 on FIG. 2. For this purpose, the surface of the trays on which the blood samples are deposited may be photosensitive.

In operation, when a blood sample, such as sample 12' in FIG. 2, is contaminated, emissions from this sample are detected by cell 33' and cause lamp 39' to be energized through terminal 41 after a predetermined delay in circuit 40 for producing a mark 42 adjacent to sample 12' when the moving belt has advanced that sample to the marking position under marker arm 24.

Other more sophisticated means may be employed to identify contaminated cells. Thus a laser with beam steering optics may be used as a marking source and operated to mark the cell or cells of interest without delay while those cells are still illuminated by the source beam 17. Alternatively, marking may take the form of sample location information stored in a computer memory bank operationally connected to the output of receiver 19.

Figure 4:
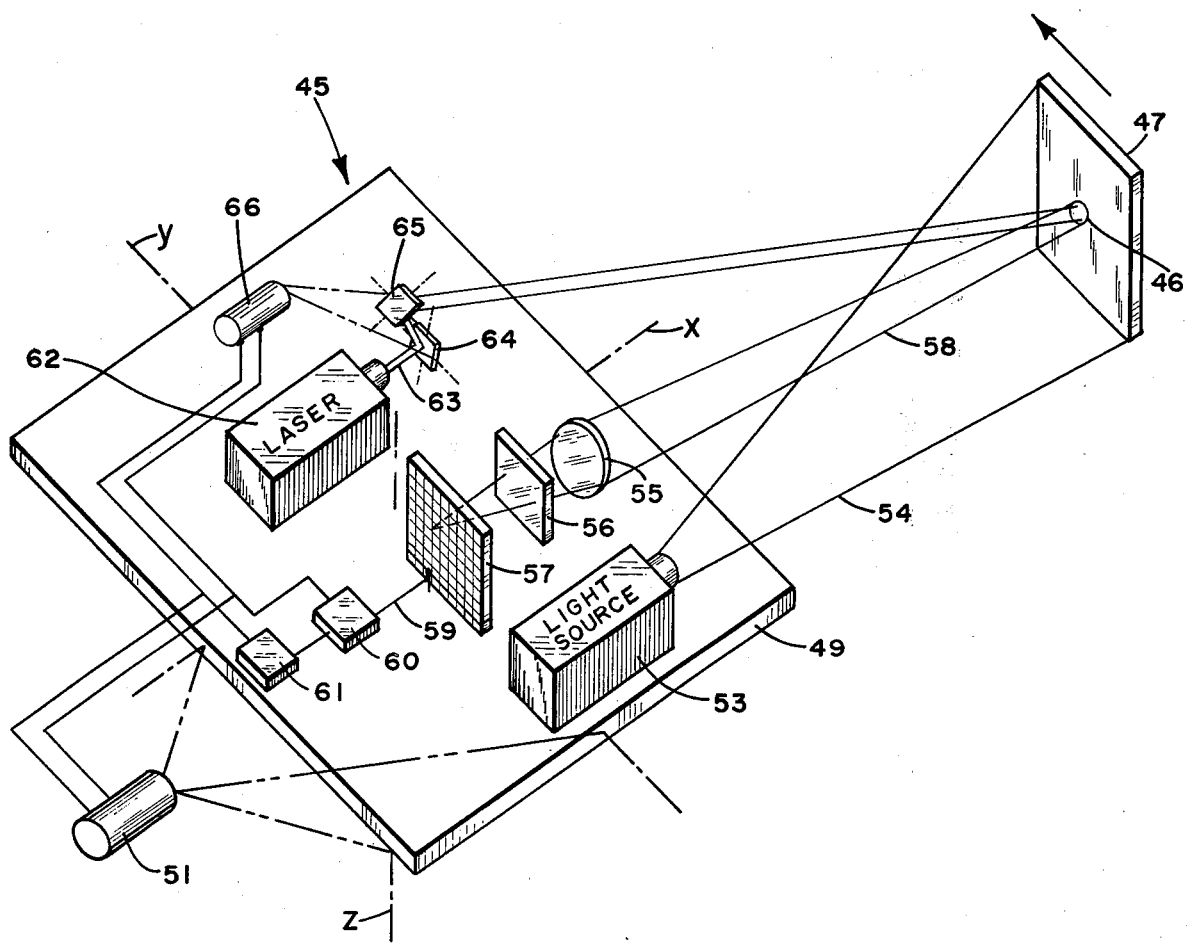
FIG. 4 is a perspective view of automatic tracking apparatus embodying this invention.

Another embodiment of the invention is the automatic tracking apparatus 45 shown in FIG. 4. The object 46 for tracking is located on a base 47 of larger area and which is movable relative to the tracking apparatus 45 as indicated by the arrow. Base 47 may be a metal plate or sheet and object 46 may comprise a spot of paint or the like, thus having a chemical constituency different from sheet 47.

Apparatus 45 comprises a platform 49 supported for pivotal movement about x, y, and z axes. Movement of the platform about these axes is caused by a servo mechanism 51 indicated as a single unit for simplicity and clarity of explanation and illustration, and mechanically connected to platform drive means, not shown, by couplings indicated in broken lines.

Base 47 is broadly illuminated by a source 53 of light which projects its beam 54 over the area of the base including object 46. By way of example, the output of source 53 may be ultraviolet light.

Also mounted on platform 49 is a lens 55, an optical filter 56 and an array 57 of photodetector cells. Lens 55, filter 56 and array 57 correspond to lens 31, filter 32 and cells 33, respectively, described above except that filter 56 is designed to pass fluoroescent radiations 58 from object 46 and to block radiations at other wavelengths. The position of incidence on array 57 of the output of filter 56 is converted into signals on line 59 representing the coordinates of such incidence which are converted by signal processors 60 and 61 into servo drive signals of the proper sense.

Servo mechanism 51 is connected to the outputs of processors 60 and 61 for steering the platform. The outputs of signal processors 60 and 61 are zero when the point of incidence of the beam on the array is at a neutral or reference location such as the center of the array. As the beam 58 from object 46 moves this point of incidence from the array center, error signals of the proper sense are generated on line 59 to cause the platform to track the object.

In addition to the normal tracking operation of platform 49 as described above, it may be desirable to utilize the error signals from processors 60 and 61 to steer an optical beam or the like from a source on platform 49 to intercept object 46 continuously as base 47 moves. To this end, mounted on platform 49 is a source 62 of light, such as a laser, having a narrow output beam 63 and movable mirrors 64 and 65 oriented to steer beam 63 so as to track object 46. Mirrors 64 and 65 are caused to move about their respective axes by a servo mechanism 66 connected to processors 60 and 61 and adapted to steer beam 63 for precise illumination of object 46 as it moves.

Alternatively, servo mechanism 51 may be manually actuated so that movement of platform 49 is independent of error signals generated by processors. In such event, automatic tracking of the object 46 by beam 63 is effected solely by the response of servo mechanism 66 to the error signals. In another modified form of the invention, servo mechanism 66 and steering mirrors 64 and 65 may be omitted entirely so that the output of laser 62 tracks object 46 through the movement of platform 49 driven by servo mechanism 51.

Figure 5:
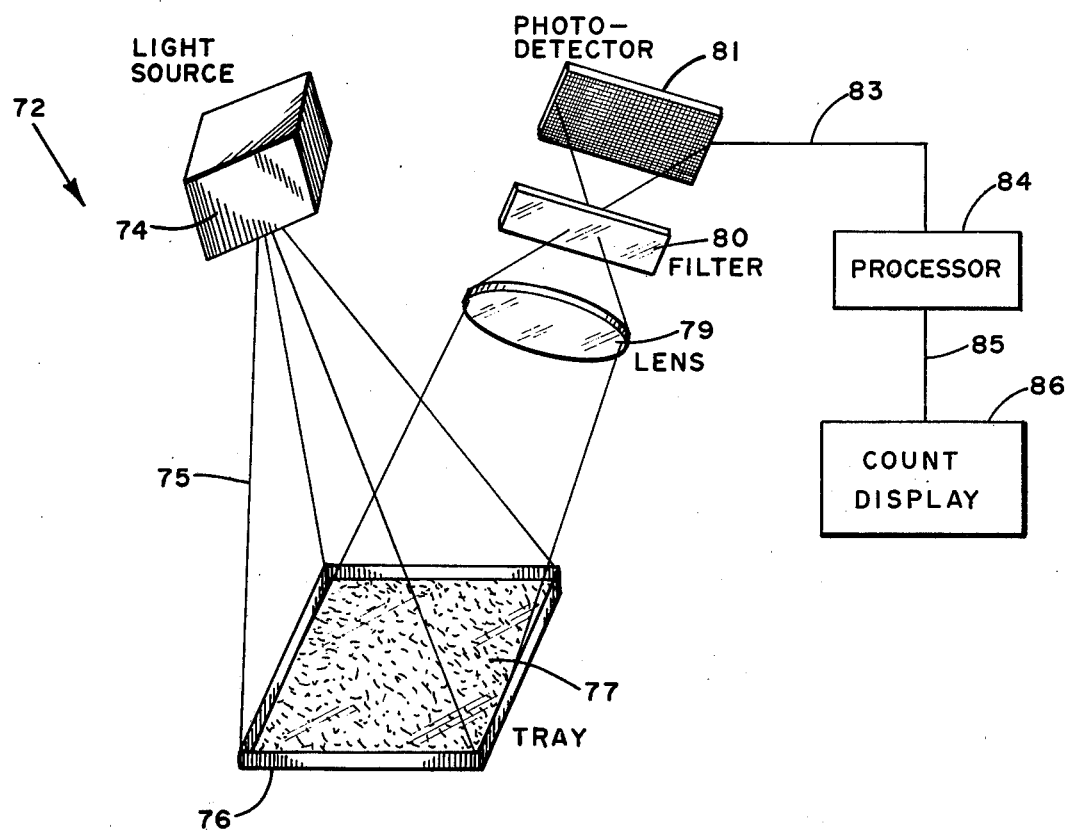
FIG. 5 is a perspective view of a system embodying this invention for counting the number of foreign particles in a predetermined area of particulate material.

Another embodiment of the invention is illustrated in FIG. 5 as quality control inspection apparatus 72 for objects in particulate form which may be contaminated with a foreign object. For example, wheat is subject to contamination with onion seeds during harvesting and a count of the number of onion seeds in a sampling of wheat kernels is desirable to provide a measure of this contamination. Apparatus 72 comprises a source 74 of light such as ultraviolet light, which produces a beam 75 that illuminates a tray 76 of particulate material 77 being examined. A lens 79 focuses emissions from tray 76 through an optical filter 80 to an array 81 of photodetector cells so that substantially all of the cells in the array are exposed to the filter output. Filter 80 is selected to pass fluoroescent emissions from the contaminant, such as the onion seed in the foregoing example, and to block all other emissions. The output of filter 80 on array 81 illuminates a number of cells corresponding to the number of contaminants in the sample. The output from array 81 on line 83 contains a count of the number of energized cells and is connected to a processor 84 comprising a logic circuitry for converting the count signal from array 81 into signal for energizing a count display 86. This provides an instantaneous readout of the contamination level in any desirable form.

The invention in its broadest form is applicable to other situations where a defect or abnormality may be correlated with a fluoroescent signature. The foregoing descriptions of preferred embodiments of the invention are therefore given by way of example and not by way of limitation.

What is claimed is:

1. An automatic tracking system for an object having a trackable surface composed of first and second substances at different locations on the object comprising
   optical transmitter means having an output beam with a first wavelength directed toward said object whereby to illuminate all of said trackable surface with said light and cause said first and second substances to emit light at second and third wavelengths, respectively,
   a receiver responsive to light at said second wavelength and unresponsive to light at said third wavelength, said receiver having an optical transducer array capable of producing an electrical output signal corresponding to the position of incidence of said second wavelength light on said array,
   logic circuit means receiving the output of said array and deriving an error signal proportional to the deviation of said position of incidence of said first wavelength light from a reference position on said array,
   a laser adapted to produce an output beam and
   a steering mechanism for said laser beam,
   said beam steering mechanism being connected to said logic circuit means and being responsive to said error signal for steering said laser beam for incidence on said first substance on said object.

2. Apparatus for detecting and locating a substance having a predetermined composition comprising
   optical transmitter means having an output beam with a wavelength $\lambda_1$ directed to illuminate a wide area containing said substance whereby to cause said substance to produce fluoroescent emission at a wavelength $\lambda_0$ different from $\lambda_1$ and characteristic of the composition of said substance,
   optical receiver means comprising
      a filter disposed to receive emissions from said area and to pass emissions at wavelength $\lambda_0$ and to block emissions at other wavelengths,
      means to focus the output of said filter into a narrow beam,
      a plurality of photoelectric transducer cells arranged in adjacent rows and columns and disposed so that the output beam of said filter is incident on substantially less than all of the cells and thereby producing an electrical output corresponding to the relative position of incidence of said beam on said array, and
   means for utilizing the output of said array to identify the location of said substances comprising a laser adapted to produce an output beam, means to steer said output beam into intercept alignment with said substance including motor means and optical means coupled thereto, and means to connect the output of said array to said motor means.

3. A method of searching for, identifying and marking the location of an object having a composition characterized by a fluorescence emission wavelength $\lambda_2$ when illuminated by light having a wavelength $\lambda_1$ comprising the steps of
   illuminating the search area with light having a wavelength $\lambda_1$,
   directing a receiver toward the illuminated search area and blocking all inputs to the receiver other than emissions having a wavelength $\lambda_2$,
   focusing said $\lambda_2$ input emissions to the receiver into a point of relatively small area incident on an array of photodetector cells and producing an electrical output from said array corresponding to the coordinates of said point of incidence and thereby the coordinates of said object in the search area relative to said receiver, and
   applying said array output to beam transmitter means and causing the transmitter beam to be directed toward said object.

4. An automatic tracking system for an object having a trackable surface composed of first and second substances at different locations on the object comprising
   a source of ultraviolet light directed toward said object whereby to illuminate substantially all of said trackable surface with said light and cause said first and second substances to emit light at first and second wavelengths, respectively,
   a receiver responsive to light at said first wavelength and unresponsive to light at said second wavelength, said receiver having an optical transducer array comprising a plurality of photodetector cells arranged in adjacent columns and rows, and a lens positioned relative to said array to focus light at the first wavelength to a point incident on said array whereby to produce an electrical output signal corresponding to the coordinates of said point of incidence, logic circuit means receiving the electrical signal output of said array and deriving an error signal proportional to the deviation of said position of incidence of said point from a reference position on said array, a laser adapted to produce a narrow output beam, and a steering mechanism for said laser beam,
said beam steering mechanism being connected to said logic circuit means and being responsive to said error signal for steering said laser beam into incidence with said first substance on said object.

* * * * *